United States Patent [19]

Kawahara et al.

[11] Patent Number: 4,724,081
[45] Date of Patent: Feb. 9, 1988

[54] PROCESS AND APPARATUS FOR SEPARATION BY LIQUID CHROMATOGRAPHY

[75] Inventors: Akio Kawahara; Hiroto Sugeno; Shuji Ishii; Hiroshi Saito, all of Tokyo, Japan

[73] Assignee: Soken Kagaku Kabushiki Kaisha, Tokyo, Japan

[21] Appl. No.: 856,764

[22] Filed: Apr. 28, 1986

[51] Int. Cl.$^4$ ............................................. B01D 15/08
[52] U.S. Cl. .................................. 210/659; 210/198.2
[58] Field of Search ................. 210/659, 198.2; 55/67, 55/386; 422/70

[56] References Cited

U.S. PATENT DOCUMENTS

| | | | |
|---|---|---|---|
| 3,458,437 | 7/1969 | Ouano | 210/659 |
| 3,686,117 | 8/1972 | Lauer | 210/659 |
| 4,204,952 | 5/1980 | Snyder | 210/659 |
| 4,267,054 | 5/1981 | Yoritomi | 210/659 |
| 4,274,967 | 6/1981 | Snyder | 210/659 |
| 4,314,823 | 2/1982 | Rich | 210/198.2 |
| 4,454,043 | 6/1984 | Ting | 210/659 |
| 4,551,288 | 11/1985 | Kelly | 210/198.2 |

OTHER PUBLICATIONS

Kirkland, Introduction to Modern Liquid Chromatography, John Wiley & Sons, Inc., New York, 1979, pp. 519-520.

Primary Examiner—Ernest G. Therkorn
Attorney, Agent, or Firm—Koda and Androlia

[57] ABSTRACT

A separation process by liquid chromatography, which comprises sending a mixture sample in a large amount together with a liquid mobile phase to at least one column, into which a packing having a large particle size has been charged, to preliminarily fractionate the components of the mixture, taking out fractions containing objective components from the eluate from the first column, and recycling said fractions within a loop provided with at least one second column, into which a packing having a large particle size has been charged, to separate precisely the objective components.

According to this process, it is possible to separate economically objective components from the sample loaded in a large amount.

2 Claims, 11 Drawing Figures

PROCESS AND APPARATUS FOR SEPARATION BY LIQUID CHROMATOGRAPHY

BACKGROUND OF THE INVENTION

1. Technical Field

The present invention relates to a separating process by liquid chromatography, more particularly an industrial process for separating a large amount of samples by liquid chromatography, and to an apparatus therefor.

2. Prior Art

Liquid chromatography using liquid as a mobile phase is being generally used as an analytical method in various fields since a sample in a very small amount can be readily analyzed rapidly and with high precision and with good reproducibility by this technique. A liquid chromatographic analysis apparatus comprises a liquid transfer part, a sample injecting part, a separating part (column) and a detecting part. In this chromatographic apparatus, a liquid as a mobile phase is previously caused to flow by the liquid transfer part, and a sample is then injected from the injecting part. The components in the sample are eluted in order from those having weaker affinity for the stationary phase to those having stronger affinity therefor. These eluates are detected by the detector for profiling a chromatogram. Applications of analytical liquid chromatography to separation system on an industrial scale only by increasing the diameter of the column have been proposed.

In analytical separation methods using liquid chromatography and analytical apparatuses using the methods, fine particulate packings with a particle size of 5 $\mu$m or less are generally used, and a small amount of a sample is loaded thereon. The apparatus is operated under a high pressure of 50 to 100 kg/cm$^2$, and the small amount of the sample loaded is separated with high precision with a small single column having several ten $\mu$m of H.E.T.P. (height equivalent of theoretical plate). On the other hand, separation using liquid chromatography on an industrial scale should be carried out while keeping the required resolving power to separate efficiently objective components taking account of the large amount of load and economy. In other words, it is necessary to separate efficiently a large amount of sample in a large column having a H.E.T.P. of several ten $\mu$m or more under a low pressure of 20 kg/cm$^2$ or less with the use of inexpensive packings having a large particle size of 10 $\mu$m or more in place of expensive fine particulate packings. Thus, conventional large-scale separating methods and apparatuses therefor wherein analytical separating methods and apparatuses therefor are only scaled up are not economical or efficient.

SUMMARY OF THE INVENTION

An object of the present invention is to provide a process for separating economically objective components from a large amount of a sample loaded while maintaining a H.E.T.P. sufficient for separation.

Another object of the present invention is to provide a liquid chromatography separation apparatus for industrial use which has a high separation performance through the use of an inexpensive packing of large particle size in spite of its rapid processing of a sample load of large quantity.

A further object of the present invention is to provide a liquid chromatography separation apparatus which can separate rapidly and efficiently under the condition of a load of a large amount of a sample while maintaining a high separation capacity.

As a result of tests and research, we have found that the aforementioned objects can be effectively achieved by constructing a multiple-column system and recycling fractions containing objective components with at least one of the columns. The present invention has been accomplished as a consequence of this finding.

In accordance with one embodiment of the present invention, an industrial separation process by liquid chromatography comprises supplying a large amount of a mixture sample together with a mobile phase liquid to at least one of first columns, in which a first packing having a large particle size has been filled, to develop the components of the mixture in the column, partially taking out fractions containing the objective components to be separated from the eluate from the first column, and recycling the aforementioned fractions within a loop equipped with at least one of second columns, in which a second packing having a large particle size has been filled, to separate the objective component from other components.

According to one of the embodiments of the present invention, a large-scale separating apparatus for separating objective components from a large amount of a mixture sample by liquid chromatography includes a preliminary fractionation line comprising at least one first column, into which a first packaging having a large particle size has been charged, an eluent bath provided through a passage at the side of the upper stream of the first column, a sample-injecting valve provided in a passage between the first column and the eluent bath, a sample bath communicated with the sample-injecting valve, a first fraction collector provided through a passage at the downstream of the first column, a first detector provided in a passage between the first column and the first fraction collector, a liquid transfer device provided in a passage, and a pre-cut valve provided in a passage between the first column and the first fraction collector for taking out main fractions containing objective components; and a recycling line comprising a second column charged with a second packing having a large particle size, which column is to be communicated through a passage with the pre-cut valve in the aforementioned preliminary fractionation line on taking out the main fractions, a second fraction collector provided through a passage on the downstream side of the second column, a second detector provided in a passage between the second column and the second fraction collector, a recycling valve for turning eluates from the second detector to the inlet of the second column on recycling procedure and causing the objective component to flow into the second fraction collector after completion of separation, and a liquid transfer device provided in a passage between the recycling valve and the inlet of the second column.

According to another embodiment of the present invention, a large-scale separating apparatus for separating objective components from a large amount of a mixture sample by liquid chromatography comprises at least one first column, into which a first packing having a large particle size has been charged, at least one second column, in which a second packing having a large particle size has been charged, a column changing valve provided through passages at the side of upper stream of the first column and the second column, a pre-cut valve provided on the downstream side of the first column and the second column through respective passages and communicated with the second column upon the taking out of the objective fractions, an eluent tank provided through a passage on the upstream side of the column changing valve, a sample injecting valve provided in a passage between the column changing valve and the eluent tank, a sample tank communicated with the sample injecting valve, a fraction collector provided through a passage on the downstream side of the pre-cut valve, a detector provided at the downstream side of the first column and the second column, a recycling valve which is provided at the position where the passage between the pre-cut valve and the fraction collector intersects the passage between the eluent tank and the sample injecting valve and makes a passage from a column communicating with a passage to the column in recycling procedure, a liquid transfer device provided in a passage, and a central passage which directly connects the pre-cut valve to the column changing valve.

The present invention is capable of affording the following advantages.

(a) According to the present invention, at least two kinds of columns can be used, and optimum separation can be carried out with respective columns. In other words, a sample can be preliminarily fractionated in the first column, and main fractions containing objective components in high amounts can be taken out. More precise separation can be carried out by repeatedly recycling the main fractions in the second column.

(b) In the first column, only preliminary fractionation is conducted, so that expensive particulate packings are not required and inexpensive packings having a large particle size can be used. In the second column, the main fraction containing the objective component in a high amount is developed by recycling procedure, so that it is not essentially necessary to use expensive packings, and it is sufficient to use inexpensive packings having a large particle size.

As described above, packings having a large particle size can be used, so that the operation can be conducted at a low pressure of 60 kg/cm$^2$ or less. Furthermore, since the operation can be conducted at such a low pressure, pressure resistance is not required for a separating apparatus, so that a separating apparatus can be made inexpensively. The present invention affords economy.

(c) In the present invention, the objective component in the first column is concentrated to a high degree, and a sample even in a large amount can be treated in one batch. Then the main fraction thus concentrated is repeatedly developed in the second column, so that it is possible to conduct separation with high precision and to obtain the objective component with high purity. Thus, samples in great amounts can be separated with high precision.

(d) If a sample is developed in situ by recycling it in a column, it is not possible to obtain high separability due to the overlap of the first peak with later peaks. In the present invention, the main fraction contains only the objective component and components adjacent to the peak of the objective component, so that it is possible to recycle the main fraction with a column.

The main fraction is recycled in the second column, but the eluent is not used as for the other fractions, so that a large saving can be made in the total amount of the eluent used, and the cost for separating samples can be reduced.

DETAILED DESCRIPTION OF THE INVENTION

Separating Method

Figure 1:
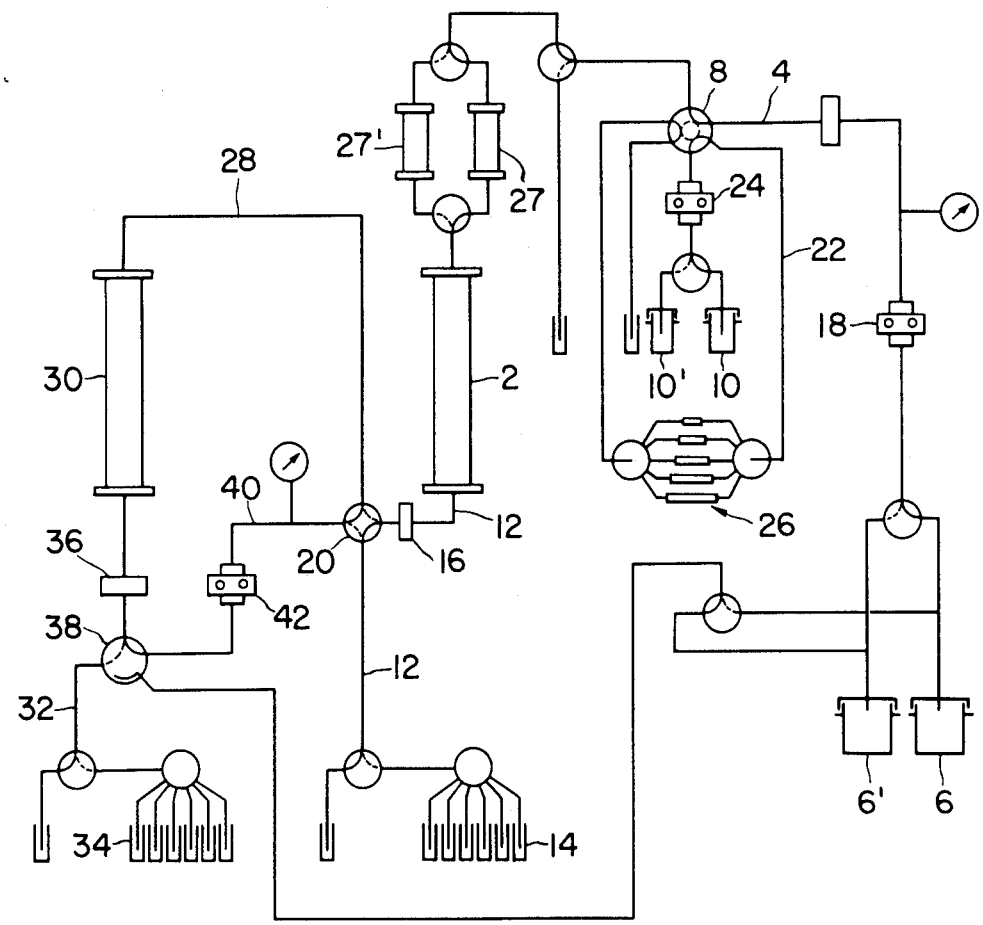
FIG. 1 is a flow-sheet illustrating an embodiment of the separating apparatus according to the present invention.

The separating method according to the present invention uses a combination of at least a first column and a second column, wherein development is carried out in the first column to remove unnecessary fractions by preliminary fractionation and to increase largely the content of the objective component, then the main fraction (main eluate) is further developed on the second column to carry out more precise separation.

In the separating method in accordance with the present invention, the principle of liquid chromatography is used. As the liquid chromatography, there are partition chromatography by separation mechanism based on the difference of the solubilities into a stationary phase and a mobile phase, adsorption chromatography by the separation mechanism based on the difference of adsorptivities to an adsorbent of the stationary phase, ion-exchange chromatography by the separation mechanism based on the difference of ion-exchanging powers to the ion-exchanging resin of the stationary phase, gel chromatography by separation mechanism based on the permeabilities into pores on the porous particles of the stationary phase and others. Thus, the packing used in the present invention is selected according to the aforementioned classification of chromatography.

In the separating method of the present invention, a large amount of a mixture sample is supplied together with a liquid as a mobile phase to at least one first column wherein the first packing having a large particle size has been charged. The sample used in the present invention is a mixture containing a plurality of components. For instance, multi-component samples containing trace components to be separated, heat-unstable materials, isomers, etc. are advantageous in the present invention. In the present invention, the amount of the sample to be treated per batch is preferably a large amount, e.g., from several tens of grams to several hundreds of grams.

The liquid used as the bomile phase in the present invention includes hexane, benzene, ethyl acetate, methyl acetate, chloroform, tetrahydrofuran, water, formamide, acetonitrile, methanol, ethanol, etc. It is selected by taking into account the recovery of the solvent, compatibility with the sample, the detector and the packing, and the like.

In the first column according to the present invention, a sample is developed to carry out preliminary fractionation thereof. A plurality of the first column may be used, if necessary, in series and/or in parallel. The internal diameter of the column is, for example, several mm to several hundreds of mm, preferably 10 to 600 mm. This is because a large amount of a sample can be treated in one batch with the use of a column having a large internal diameter. The first packing charged in the first column has a larger particle size as compared with that of a packing for analytical or experimental use. The first packing has a particle size exceeding 10 μm, preferably 30–500 μm, since the cost of a packing can be reduced by the use of a packing having larger particle size and a large amount of a sample can be treated at low pressure thereby. It is not always necessary to separate respective components in the first column because more precise separation is carried out in the second column although the separation power of the first column is reduced by the use of a packing having a large particle size. The material of the packing includes the one usually used in chromatography, such as silica, alumina, polystyrene gel, active carbon, various porous polymers, other chemically bonded packings, etc.

In the present invention, liquid sending pressure can be reduced to, for example, less than 60 kg/cm$^2$, preferably less than 20 kg/cm$^2$, because a packing having a large particle size is used.

In the separation method according to the present invention, the fraction containing the objective component to be separated (main fraction) is taken out from the eluate from the first column wherein respective components have been developed. The main fraction can be taken out by a procedure such that peaks of a chromatogram are detected by a detector or the retention time of the main fraction is preliminarily measured by a preliminary test.

The detector which can be used in the present invention includes conventional types of ultraviolet absorption photometer (UV), differential refractometer (RI), fluorophotometer (FP), flame ionization detector (FID), infrared absorption photometer (IR), polarograph, electric conductivity detector, thermal conductivity detector, radioactivity counter, etc.

In the separating method according to the present invention, the main fraction is recycled in a loop equipped with at least one of the second column, into which the second packing having a large particle size has previously been charged, to separate more precisely the objective component from other components.

The mobile phase used in the second column for recycling may be the same mobile phase as that used in the first column or a different one. The examples of the phase include hexane, benzene, ethyl acetate, methyl acetate, chloroform, tetrahydrofuran, water, formaldehyde, acetonitrile, methanol, and ethanol. The mobile phase is selected by taking into account the recovery of the solvent, compatibility with the sample, the detector, the packing and the like.

The second column according to the present invention is used for the development of the main fraction to carry out more precise separation. A plurality of columns can be used as the second column, if necessary, in series and/or in parallel. The inner diameter of the column is, for example, several mm to several hundreds of mm, preferably of the order of 10 to 600 mm. The packing charged into the second column is that having the same particle size and pore diameter as, or different particle size and pore diameter from, those of the first packing. The packing has a larger particle size as compared with that usually used in ordinary analysis. The particle size of the second packing exceeds 10 μm, preferably 30 to 500 μm. If a packing having a large particle size used, the cost of the packing can be reduced and a large amount of a sample can be treated at low pressure. When a packing having a large particle size is used, the resolving power of the second column itself is decreased, but the second column itself is not necessarily required to have a high resolving power because a sample is recycled. The kind of the second packings may be the same as or different from those of the first packings. Examples of the packings include those used in ordinary chromatography such as silica, alumina, polystyrene gel, active carbon, various porous polymers and other chemically bonded packings.

The recycling of the main fraction in the second column is carried out until satisfactory separation is accomplished. Thus, the recycling number varies depending upon the components in the main fractions, and the resolving powers of columns. For the purpose of observing the degree of separation, a detector may be provided on the downstream side of the second column.

The objective component having been separated in the recycling loop is taken out from the loop. Taking out of the component can also be monitored by the aforementioned detector. The detector which can be used in the present invention includes conventional ones such as ultraviolet absorption photometer (UV), differential refractometer (RI), fluorophotometer (FP), flame ionization detector (FID), infrared absorption photometer (IR), polarograph, electric conductivity detector, thermal conductivity detector, radioactivity counter, etc.

Separating apparatus

Embodiments of the separating apparatus according to the present invention will now be described with reference to the drawings.

FIG. 1 is a flow sheet illustrating an embodiment of the separating apparatus according to the present invention. The separating apparatus includes a preliminary fractionation line comprising a first column 2 wherein a first packing having a large particle size has been charged, eluent baths 6 and 6' provided through a passage 4 at the side of the upper stream of the first column 2, a sample injecting valve 8 provided in the passage 4 between the first column 2 and the eluent bath 6, sample baths 10 and 10' communicated with the sample injecting valve 8, a first fraction collector 14 provided through a passage 12 on the downstream side of the first column 2, a first detector 16 provided in the passage 12 between the first column 2 and the first fraction collector 14, a pump 18 provided in the passage 4, and a pre-cut valve 20 provided in the passage 12 between the first column 2 and the first fraction collector 14 and intended to take out a main fraction containing objective intended to take out a main fraction containing objective components.

In the preliminary fractionation line according to the embodiment of the apparatus, there are provided a pump 24 for the sample, a sample weighing device 26 in the passage between the sample bath 10 and the sample injecting valve, and guard columns 27 and 27' for removing contamination in the sample by adsorbing it thereon at the upper stream of the first column 2. In the apparatus according to the embodiment of the present invention, there is also included a recycling line comprising a second column 30, into which a second packing having a large particle size has been charged, and which is communicated through a passage 28 with the aforementioned pre-cut valve 20 in the preliminary fractionation line on taking out the main fraction, a second fraction collector 34 provided through a passage 32 at the downstream of the second column 30, a second detector 36 provided in the passage 32 between the second column 30 and the second fraction collector 34, a recycling valve 38 which is intended to return the eluate from the second detector to the inlet of the second column 30 on recycling procedure and to cause the respective components to flow after having been completely separated into the second fraction collector 34, and a pump 42 provided in a passage 40 between the recycling valve 38 and the inlet of the second column 30.

The operation and function of the apparatus illustrated in FIG. 1 are as follows.

Description is specifically set forth with reference to the case where the component $\beta$ is intended to be separated from a sample consisting of four components of $\alpha$, $\beta$, $\gamma$, and $\delta$.

After the separating apparatus has been prepared for operation, a sample in the sample bath 10 is supplied to the sample weighing device 26 by the pump 24 to take out a predetermined volume of the sample. The sample injecting valve 8 is then changed over. Thus, the sample weighing device 26 is communicated through the passage 4 with the eluent bath 6 and the first column 2, so that the sample in a predetermined amount is charged into the first column together with the eluent supplied from the eluent bath 6 through the pump 18. In this example of the apparatus, the sample is passed through the guard column 27 prior to being charged into the first column. The guard column is not the one for developing the sample components by chromatography but the one for removing contaminations in the sample and/or eluent. Thus, decomposition of the packing in the first column can be prevented.

Figure 2:
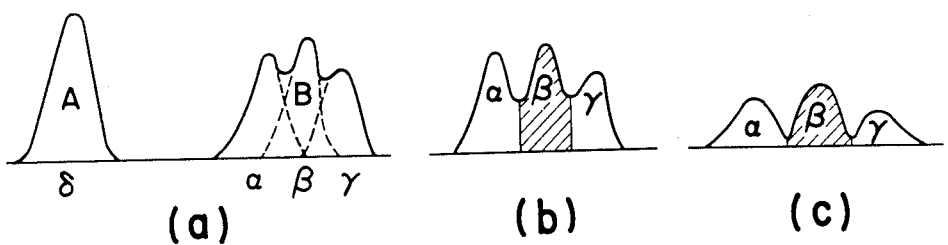
FIG. 2 is a diagram illustrating chromatograms which are obtained by the separating process of the present invention.

The sample is then developed into respective components in the first column, producing a chromatogram having two big peaks is shown in FIG. 2-a, wherein the component $\beta$ to be separated is contained in the peak B. The eluate from the first column passes through the first detector 16. The peak A is detected by the first detector 16 and supplied through the valve 20 to the first fraction collector 16. When the peak B is detected by the first detector 16, the pre-cut valve 20 is changed over and the peak B, i.e., the main fraction is charged into the second column 30 through the passage 28. After the main fraction has been taken out, the pre-cut valve 20 is again changed over to the original state. In this state, the preliminary fractionation line and the recycling line can be operated independently.

The main fraction charged into the second column is developed therein to produce peaks of $\alpha$, $\beta$ and $\gamma$ as shown in FIG. 2-b, in which peaks are partly overlapped and are not completely separated. The eluate from the second column passes through the second detector 36 to detect respective peaks. The peaks are not completely separated, and the main fraction is again charged into the second column 30 through the pump 42.

The main fraction having been developed again in the second column is separated satisfactorily into three peaks of $\alpha$, $\beta$ and $\gamma$ as shown in FIG. 2-c. The recycled eluate is passed through the second detector 36, and the respective peaks are detected. If the component $\beta$ is detected in an amount capable of being separated, the recycling valve 38 is changed over, and the respective components are separately supplied into the fraction collector 32 through the passage 34. The recycling number increases as respective components contained in the main fraction have closer relative retention times K', and the volume of the column increases.

The preliminary fractionation line is independent of the recycling line, and the residual fractions after the main fraction has been taken out are removed through the passage 12 into the fraction collector 14.

The separating apparatus according to the present invention is treated batchwise by using a plurality of columns and complicated changing of valves and the control of pumps are smoothly operated, so that it can be controlled by sequencer and a computer.

An example of an application of a microcomputer is described hereunder.

Figure 10:
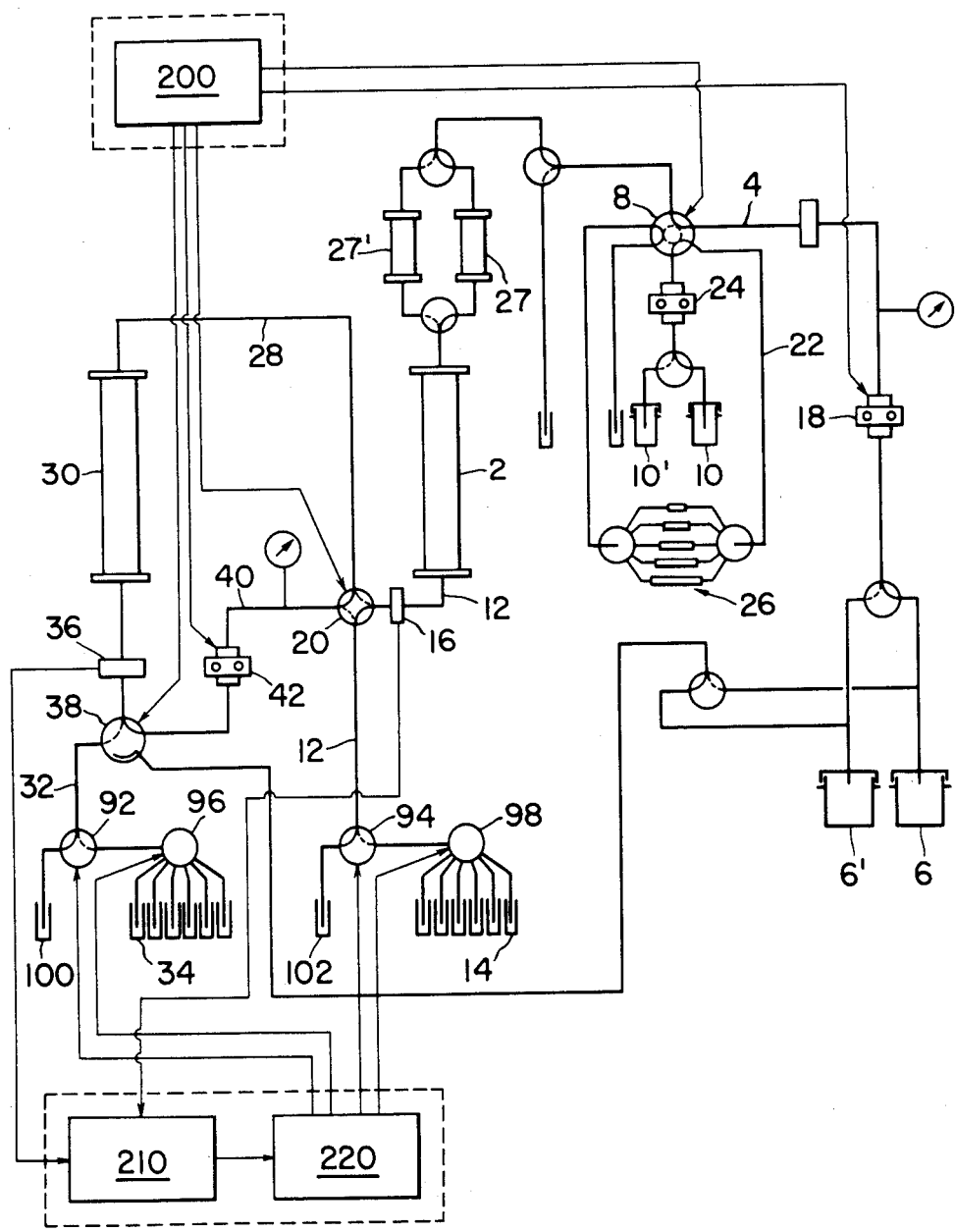
FIG. 10 is a flow-sheet illustrating an embodiment of the separating apparatus according to the present invention that includes a microcomputer.

The example of the separating apparatus as illustrated in FIG. 10 is characterized in that the sample injecting valve 8, the pre-cut valve 20 and the recycling valve 38 are changed over by respective controlling signals, that the operation states of the pumps 18, 24 and 42 respectively in the preliminary fractionation line and the recycling line are controlled according to respective controlling signals, and in that it includes first and second preparative valves 94 and 92, which are provided on the upstream sides respectively of the first and second fraction collectors 14 and 34 and are respectively changed over according to respective taking out signals, a valve 98 for changing tanks in the fraction collector 14 according to the taking out signal, a valve 96 for changing tanks in the fraction collector 34 according to the taking out signal, an operation controlling means 200 for sending controlling signals at the predetermined times, a peak judging means 210 wherein the peaks in the eluate are judged by the detection signals from the first detector 16 and the second detector 36, and a taking out controlling means wherein a taking out signal is delivered according to the above-mentioned judgement.

Figure 11:
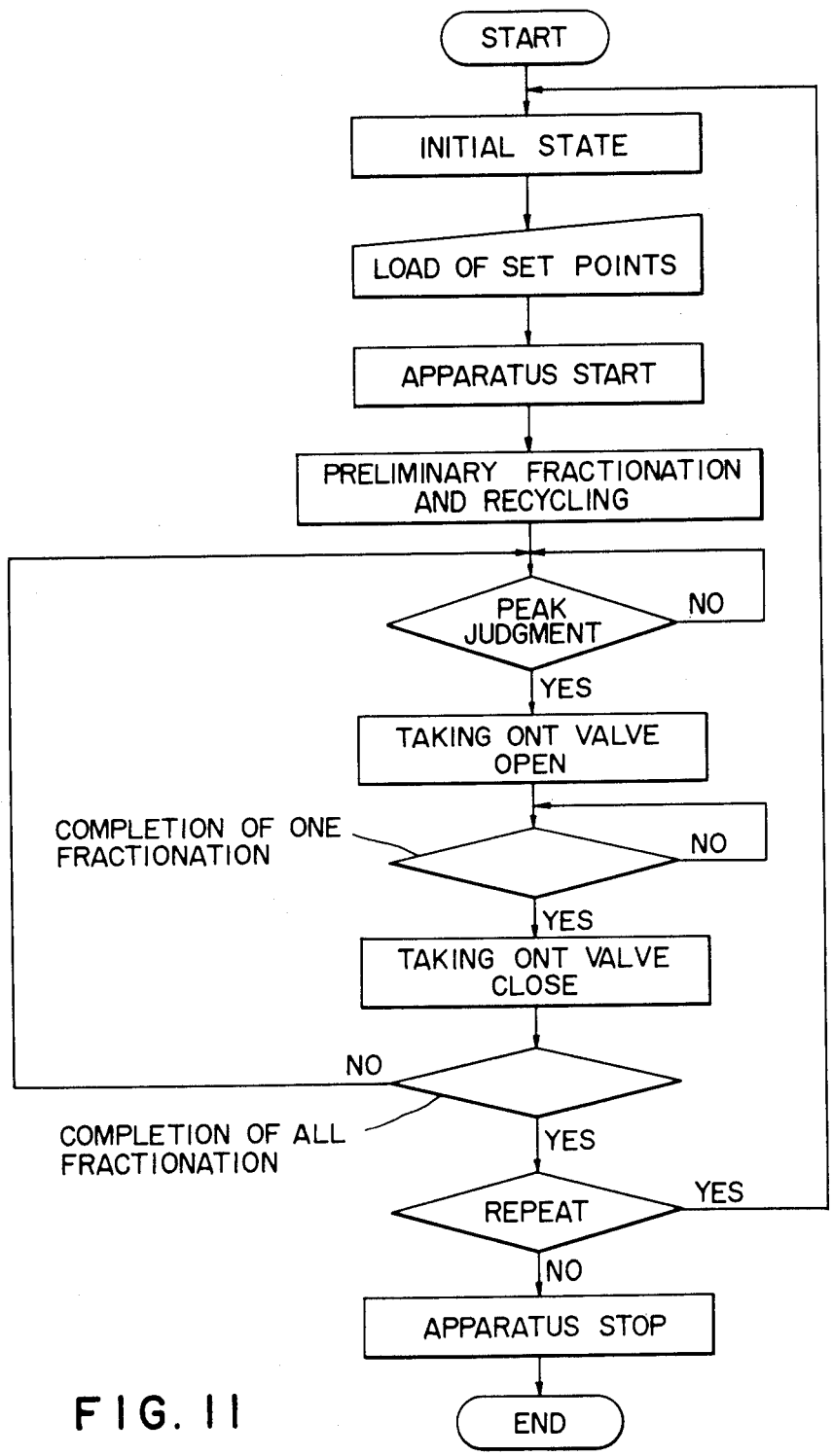
FIG. 11 is a flow chart for controlling the separating apparatus of the present invention.

A flow chart for controlling the separating apparatus of the present invention is shown in FIG. 11.

First of all, in accordance with the controlling sequence, it is confirmed that the separating apparatus is ready to work, i.e., it is in its initial state. If the apparatus is not in such a state, it is returned to the state. Then, set points for operation control are loaded. The set points include the times when the sample injecting valve 8, the pre-cut valve 20 and the recycling valve 38 are changed over for preliminary fractionation and recycling, the times when the pumps 18, 24 and 42 in the preliminary fractionation line and recycling line are operated and stopped, standards used for the judgement of peaks after recycling, etc.

After the set points have been loaded, the apparatus starts.

The apparatus is operated as described above, and the valve changing over required for the preliminary fractionation and recycling and the starting and stopping of the pumps are controlled by the controlling signals from the operation controlling means 200 based on the loaded set points.

After the preliminary fractionation and/or recycling have been completed, the peaks of the eluates are judged at the peak judging means 210 based on the predetermined standards by the detecting signals from the first detector 16 and/or the second detector 36.

If the peak is not the one to be separated, the fraction is caused to flow to a drain without being taking out, and the next peak is judged. If the peak is the one to be separated, the taking out valves 92 or 94 are opened, and at the same time the tanks in the fraction collector are changed by the valves 96 or 98.

When the judgement as to whether taking out has been completed or not is carried out according to the detecting signals of the detectors, and the judgement of the completion is made, the fractionating valve is closed.

If the taking out of the fraction of the eluate from the column is not yet completed, the judgements of next peaks are again started. If the fraction has been taken out, the judgement as to whether the above-mentioned separation is to be repeated with respect to the next batch or not is carried out. If repeated separation is required, the apparatus is returned to the initial state. If no repeat is required, the apparatus is stopped and the separation control is completed.

Figure 3:
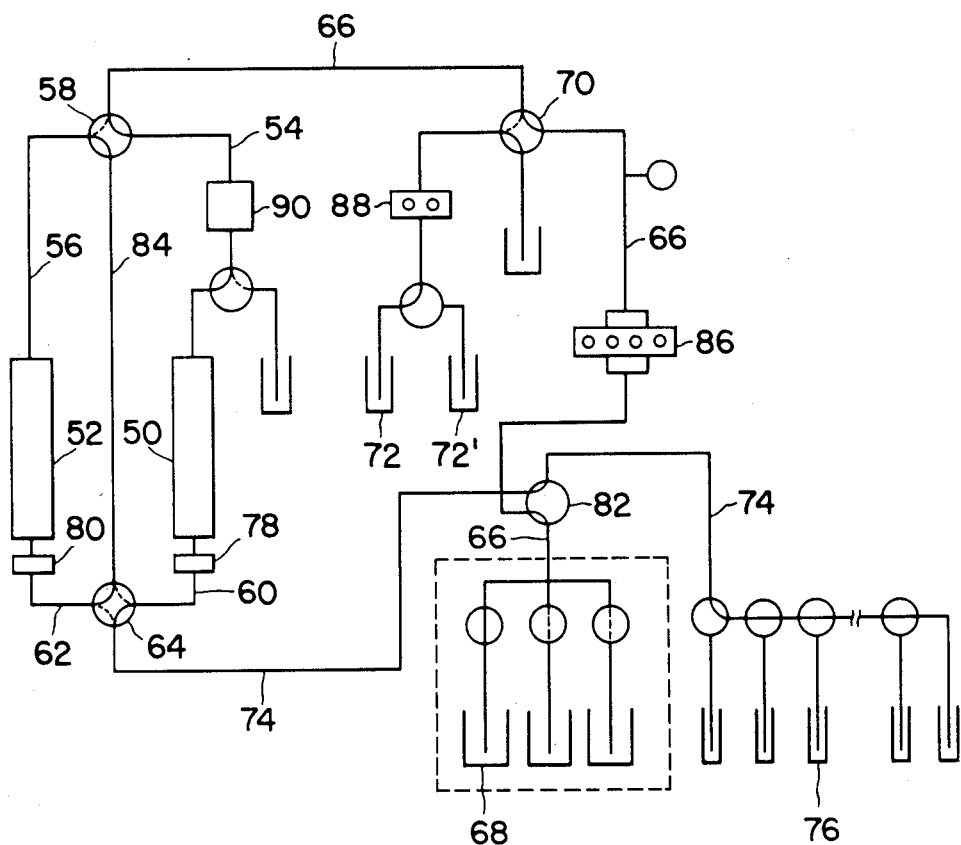
FIG. 3 is a flow-sheet illustrating another embodiment of the separating apparatus according to the present invention.

FIG. 3 is a flow sheet illustrating another embodiment of the separation apparatus according to the present invention. The apparatus comprises at least one first column 50, in which a first packing having a large particle size has been charged, at least one second column 52, in which a second packing having a large particle size has been charged, a column changing valve 58 provided through passages 54 and 56 respectively on the upstream sides of the first column 50 and the second column 52, a pre-cut valve 64 provided on the downstream side of the first column 50 and the second column 52 through respective passages 60 and 62 and causing the outlet of the first column 50 to communicate with the inlet of the second column 52 on taking out of the main fraction containing the objective component, an eluent bath 68 provided through a passage 66 at the side of the upper stream of the column changing valve 58, a sample injecting valve 70 provided in the passage between the column changing valve 58 and the eluent bath 68, sample tank(s) 72 (and 72') communicated with the sample injecting valve 70, a fraction collector 76 provided at the side of downstream of the pre-cut valve 64 through a passage 74, detectors 78 and 80 provided at the side of downstream of the first column 50 and the second column 52, a recycling valve 82 provided at the position where the passage 66 intersects the passage 74 and causing the passage 74 from the column to communicate with the passage 66 to the column on recycling, a central passage 84 which directly connects the pre-cut valve 64 and the column changing valve 58, and a pump 86 provided in the passage.

The separating apparatus further includes a sample pump 88 in the passage between the sample injecting valve 70 and the sample bath 72 and a guard column 90 on the upstream side of the first column 50.

The operation and function of the separating apparatus illustrated by the flow sheet of FIG. 3 are as follows.

After the separating apparatus has been prepared for operation, a sample in the sample bath 10 is supplied in a predetermined amount to the first column 50 from the sample injecting valve 70 by the sample pump 88. The sample injecting valve 70 is changed over, and the sample is charged together with the eluent from the eluent bath 68 through the valve 82 into the first column 50. Before this charging, contaminants are removed by the guard column 90. The sample is developed in the first column 50, and the developed sample is detected by the detector 78.

Only the main fraction containing the objective component is charged through the passage 84, the valve 58 and the passage 56 into the second column 52 by changing over the pre-cut valve 64. After the main fraction has been taken out, the pre-cut valve is again changed. The initial fraction and residual fraction from the first column 50 are taken out through the valve 64 and the passage 74 into the fraction collector 76. Then the valves 58 and 64 are changed over, and the first column 52 is communicated with the pump 86. The main fraction is developed in the second column by the pump 86, and the eluted components are detected by the detector 80. The components contained in the main fraction have closer relative retention times K', so that they are separated more precisely by recycling in the loop. If the respective components eluted from the second column 52 have been confirmed to be sufficiently separated by the detector, the valve 82 is changed over, and the sample is taken out into the fraction collector 76.

The apparatus illustrated in FIG. 3 can be operated in the following manner. Taking out the main fraction from the first column into the second column is carried out in the same manner as described above, but when the main fraction has been partly eluted from the second column, the column changing valve 58 is changed over, and a fresh sample is further added to the second column 52. In the second column, the separation of the main fraction and the separation of the freshly charged sample proceed simultaneously. The respective components separated from the main fraction which has been eluted from the second column is taken out into the fraction collector 76, while only the main fraction referring to the freshly charged sample is taken out through the valves 64 and 58 into the first column and then a fresh sample is charged into the first column. The same procedure is repeated sequentially.

EXPERIMENTAL EXAMPLES

In order to indicate more fully the nature and utility of this invention, the following specific examples of practice are set forth, it being understood that these examples are presented as illustrative only and are not intended to limit the scope of the invention.

EXAMPLE 1

In an apparatus represented by a flow sheet as illustrated in FIG. 1, a recycling test using a standard sample was carried out under the following conditions.

| Experimental conditions | |
| --- | --- |
| Sample: | benzene (B) + naphthalene (N) |
| Pump size: | 2 ml |

| Experimental conditions | |
|---|---|
| Eluent: | methanol (95%) + water (5%) |
| Columns: | First column 30φ × 300 l/mm |
| | Second column 30φ × 500 l/mm |
| Packings: | First column octadecylsilane (ODS) 10–2 μm |
| | Second column ODS 40–64 μm |
| Flow velocity: | 2.3 cm/min. |
| Detection: | UV detector (λ = 254 nm) |

The experimental procedures were followed as described above, and after partially cutting the sample, it was subjected to recycling in the second column.

Figure 4:
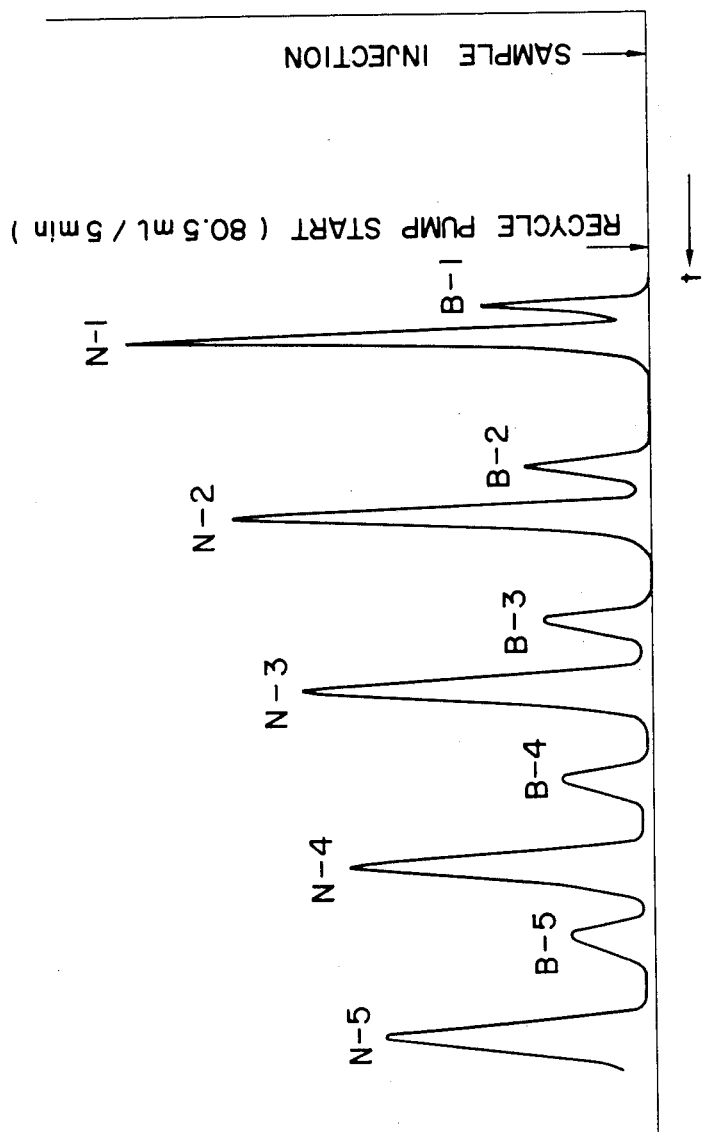
FIG. 4 is a chromatogram illustrating the result of the resolving property of the column recycling in Example 1.

The result of the recycling is shown in FIG. 4. In the figure: B-1 to N-1 represents the elution curve prior recycling; B-1 to N-2 represents the elution curve after one recycling; B-3 to N-3 represents the elution curve after recycling twice; B-4 to N-4 represents the elution curve after three recyclings; and B-5 to N-5 represents the elution curve after four recyclings. From this result, it is found that the number of recyclings can be increased by recycling only the substances having closer relative retention values. The numbers of theoretical plates are shown in Table 1.

TABLE 1

| | Number of theoretical plate | | Number of theoretical plate |
|---|---|---|---|
| B-1 | 2625 | N-1 | 2432 |
| B-2 | 3304 | N-2 | 3222 |
| B-3 | 4287 | N-3 | 4216 |
| B-4 | 4908 | N-4 | 5068 |
| B-5 | 6027 | N-5 | 5653 |

From Table 1, it can be seen that as the number of recyclings is increased, the number of theoretical plates is also increased. Furthermore, the amount of the eluent used was about ¼ as compared with the amount of the eluent required in the absence of recycling procedure.

EXAMPLE 2

The experiment of separating arachidonic acid (AA) from eicosapentaenoic acid (EAP) in a sample of a distilled sardine oil was carried out in an apparatus having a flow system as illustrated in FIG. 1 under the following conditions:

| Experimental conditions | |
|---|---|
| Sample: | distilled sardine oil |
| Sample size: | 2.5 ml |
| Eluent: | methanol (100%) |

Other conditions were the same as those specified in Example 1.

Figure 5:
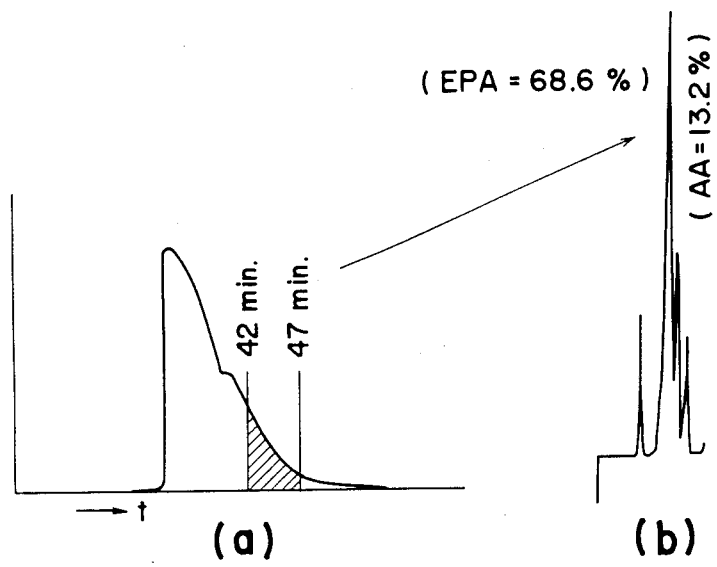
FIG. 5 is a chromatogram after elution from the second column in Example 2.
Figure 6:
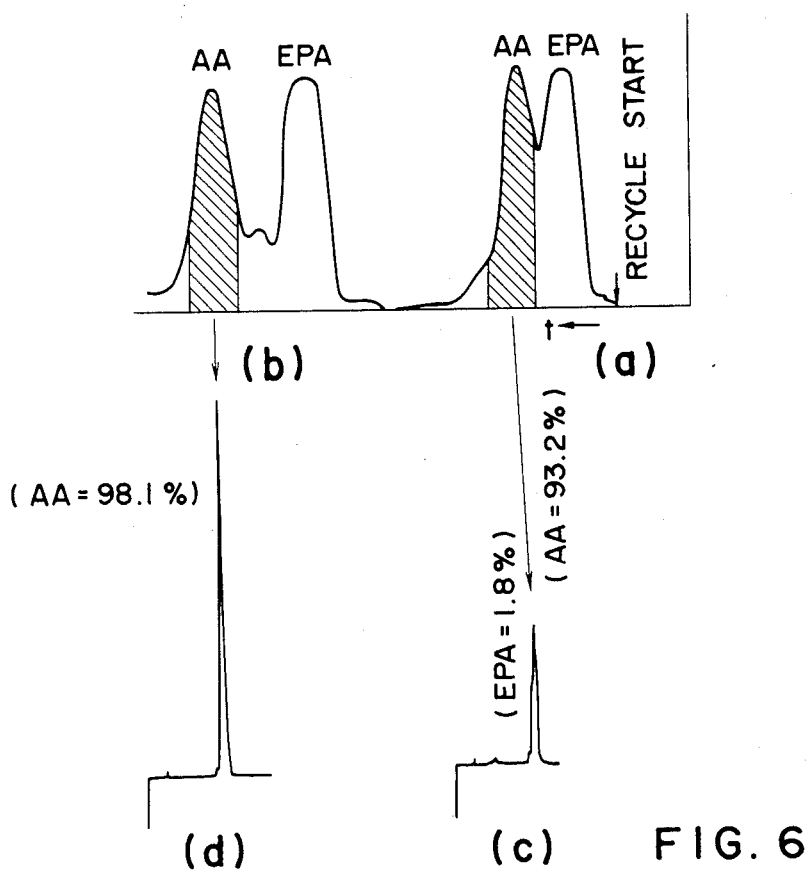
FIG. 6 is a chromatogram after recycling in the second column.

The results are shown in FIGS. 5 and 6. FIG. 5-a illustrates the separation state of the sample eluted from the first column after the sample has been loaded on the first column in an excessive amount. The only part of the peak that may be presumably considered as the AA part (illustrated by slant lines) is further loaded on the second column. FIG. 6-a illustrates the separation state of the sample eluted from the second column. The separation is not as satisfactory at this point of time as to be taken out with high purity. FIG. 6-b illustrates the result of recycling with the second column. The purity and recovery of AA are shown in Table 2.

TABLE 2

| | On eluting from the first column | On eluting from the second column | After recycling |
|---|---|---|---|
| Purity (%) | 66 | 93 | 98 |
| Recovery (%) | 66 | 58 | 56 |

The results of analysis of the raw material (sardine oil) and fractionated AA by high performance liquid chromatography (HPLC) are illustrated in the drawings. FIG. 5-b illustrates the result of analysis of the raw material, FIG. 6-c illustrates the result of analysis of the AA peak eluted from the second column and FIG. 6-d illustrates the result after recycling. In the FIGS, values within parentheses represent the purities of AA or EPA.

It can be seen from the results that AA and EPA can be readily separated.

EXAMPLE 3

The cis and trans isomers of a sample of synthetic vitamin K as an equimolecular mixture of the cis and trans isomers were separated with an apparatus having the flow system illustrated in FIG. 1.

The analytical condition was as follows:

| Sample: | synthetic vitamin K, 50% cis/50% trans |
|---|---|
| Sample amount: | 13.0 g |
| Eluent: | 98% hexane + 2% THF |
| Flow rate: | 26 ml/min. |
| First column: | 30φ × 300 l/mm |
| Second column: | 30φ × 300 l/mm |
| Packing: | 15–30 μm Si |

Figure 7:
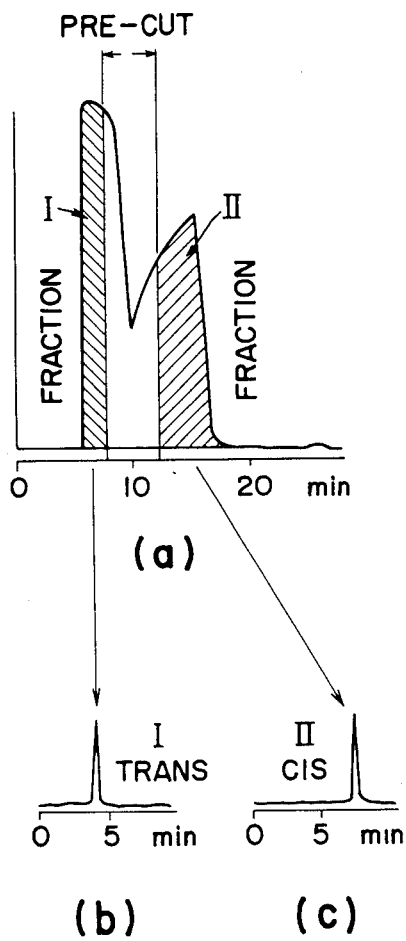
FIG. 7 is a chromatogram after elution from the first column in Example 3 wherein a two-column system is described.

The procedure of separation was as described above. Among the eluates from the first column, the fraction I of the pure trans isomer and the pure cis isomer II were fractionated, and the residual mixed fraction of the cis and trans isomers was charged on the second column. FIG. 7-a is a chromatogram of the eluate from the first column, FIG. 7-b is a chromatogram of fraction I by HPLC, and FIG. 7-c is a chromatogram of fraction II by HPLC.

Figure 8:
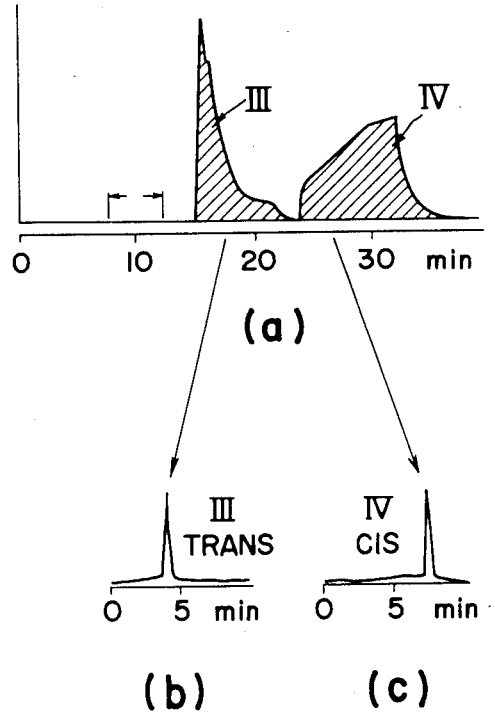
FIG. 8 is a chromatogram after elution from the second column in Example 3.

The chromatogram of the eluate from the second column is illustrated in FIG. 8. As is apparent from the chromatogram, the mixed fraction was also completely separated.

EXAMPLE 4 (COMPARATIVE EXAMPLE)

Figure 9:
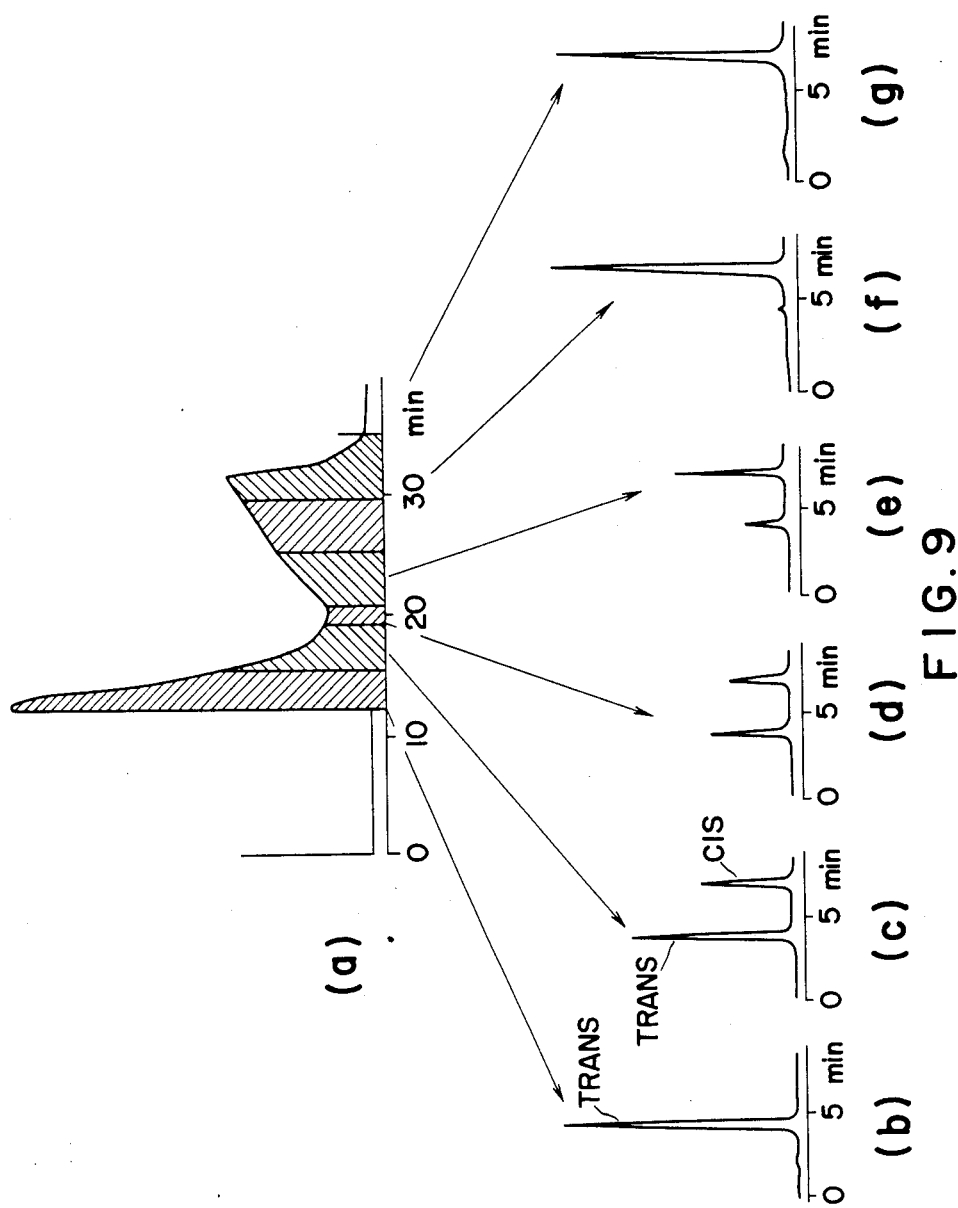
FIG. 9 is a chromatogram after elution from the second column in Example 4 wherein a single-column system is described.

The sample was separated in the same manner as in Example 3 except that the eluate from the first column in Example 3 was all directly charged into the second column without pre-cutting. The chromatogram of the eluate from the second column is illustrated in FIG. 9-a. FIGS. 9-a to 9-g are respectively chromatograms of respective fractions by HPLC.

The yields (%) of the cis and trans isomers separated in Examples 3 and 4 are shown in Table 4.

TABLE 4

| | Yield (%) | |
|---|---|---|
| | Single column | Double columns |
| Cis-isomer | 80 | 100 |
| Trans-isomer | 75 | 100 |

As is apparent from Table 4, excellent separation can be carried out with the double columns as an embodiment of the present invention.

What is claimed is:

1. A large-scale separating apparatus for separating an objective component from a large amount of a mixture sample by liquid chromatography, which has a preliminary fractionation line comprising: at least one first column, in which a first packing having a large particle size has been charged; an eluent tank provided on the upstream side of the first column; a sample injecting valve provided in a passage between the first column and the eluent bath; a sample bath communicated with the sample injecting valve; a first fraction collector provided through a passage on the downstream side of the first column; a first detector provided in a passage between the first column and the first fraction collector; a liquid transfer device provided in a liquid passage; and a pre-cut valve provided in a passage between the first column and the first fraction collector for taking out main fractions containing the objective component, and a recycling line comprising: at least one second column charged with a second packing having a large particle size, which column is to be communicated through a passage with the pre-cut valve in the aforementioned preliminary fractionation line when the main fractions are taken out; a second fraction collector provided through a passage on the downstream side of the second column; a second detector provided in a passage between the second column and the second fraction collector; a recycling valve for turning eluate from the second detector to the inlet of the second column upon recycling of the eluate and causing the objective component to flow into the second fraction collector after completion of separation; and a liquid transfer device provided in a passage between the recycling valve and the inlet of the second column; and wherein the sample injecting valve, the pre-cut valve and the recycling valve are changed over by respective controlling signals, and the operation states of the respective liquid transfer devices in the preliminary fractionation line and the recycling line are controlled according to respective controlling signals, which apparatus includes first and second fractionation valves which are respectively provided on the upstream sides of the first fraction collector and the second fraction collector and are changed over according to the respective signals for taking out samples, an operation controlling means from which controlling signals are sent out at predetermined times, a peak judging means for judging the peaks in the eluate by the detection signals respectively sent from the first detector and the second detector, and a controlling means for taking out the component which sends out taking out signals according to said judgments.

2. A process for separation by the apparatus as defined in claim 1 which comprises:
   loading the predetermined times and predetermined standards into the operation controlling means and the peak judging means, respectively in initial state of the apparatus;
   operating the sample injecting valve, the pre-cut valve, the recycling valve and the liquid transfer devices in the preliminary fractionation line and the recycling line by respective controlling signals from the operation controlling means; and
   judging the detecting signals of the peaks of eluates from the first detector and/or the second detector at the peak judging means based on the predetermined standards whereby, if the peak is not the one to be separated, the fraction corresponding to the peak is caused to flow to a drain without being taken out and, if the peak is the one to be separated, the fraction corresponding to the peak is taken out into a tank of the fraction collector.

* * * * *